United States Patent
Anderheggen et al.

(10) Patent No.: US 10,596,096 B2
(45) Date of Patent: Mar. 24, 2020

(54) AGENTS FOR GENTLY OXIDATIVELY LIGHTENING KERATIN-CONTAINING FIBERS

(71) Applicant: Henkel AG & Co. KGaA, Duesseldorf (DE)

(72) Inventors: Bernd Anderheggen, Moenchengladbach (DE); Konstantin Goutsis, Juechen (DE)

(73) Assignee: Henkel AG & Co. KGaA (DE)

( * ) Notice: Subject to any disclaimer, the term of this patent is extended or adjusted under 35 U.S.C. 154(b) by 537 days.

(21) Appl. No.: 15/149,250

(22) Filed: May 9, 2016

(65) Prior Publication Data

US 2016/0331664 A1    Nov. 17, 2016

(30) Foreign Application Priority Data

May 12, 2015    (DE) .................. 10 2015 208 788

(51) Int. Cl.
| | |
|---|---|
| *A61Q 5/08* | (2006.01) |
| *A61K 8/73* | (2006.01) |
| *A61K 8/23* | (2006.01) |
| *A61Q 5/10* | (2006.01) |
| *A61K 8/22* | (2006.01) |
| *A61K 8/44* | (2006.01) |
| *A61K 8/55* | (2006.01) |

(52) U.S. Cl.
CPC ................ *A61K 8/731* (2013.01); *A61K 8/22* (2013.01); *A61K 8/23* (2013.01); *A61K 8/44* (2013.01); *A61K 8/55* (2013.01); *A61Q 5/08* (2013.01); *A61Q 5/10* (2013.01); *A61K 2800/51* (2013.01); *A61K 2800/88* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 5,294,436 A * | 3/1994 | Cope ................. | A61K 8/22 132/208 |
| 5,635,167 A | 6/1997 | Said et al. | |
| 6,302,920 B1 | 10/2001 | Lorenz et al. | |
| 9,789,052 B2 * | 10/2017 | Anderheggen .......... | A61Q 5/08 |
| 2005/0008591 A1* | 1/2005 | Nocker .................. | A61K 8/22 424/62 |
| 2012/0315236 A1* | 12/2012 | Goutsis .................. | A61Q 5/08 424/62 |
| 2016/0058688 A1* | 3/2016 | Anderheggen .......... | A61Q 5/08 132/208 |
| 2016/0158125 A1 | 6/2016 | Neuba et al. | |

FOREIGN PATENT DOCUMENTS

| | | |
|---|---|---|
| EP | 1714634 A1 | 10/2006 |
| EP | 2471502 A1 | 7/2012 |

OTHER PUBLICATIONS

European Search Report (16163487.8) dated Sep. 15, 2016.

* cited by examiner

*Primary Examiner* — Jyothsna A Venkat
(74) *Attorney, Agent, or Firm* — James J. Cummings

(57) ABSTRACT

Agents for lightening keratinic fibers include at least two preparations (A) and (B) packaged separately from one another, of which preparation (A) includes at least one persulfate, a polysaccharide and a complexing agent, and preparation (B) includes at least one oxidizing agent.

3 Claims, No Drawings

AGENTS FOR GENTLY OXIDATIVELY LIGHTENING KERATIN-CONTAINING FIBERS

FIELD OF THE INVENTION

The present invention generally relates to agents for oxidatively changing color in the cosmetics sector, which are particularly suitable for lightening keratinic fibers, in particular human hair.

BACKGROUND OF THE INVENTION

Changing the shape and color of hair represents an important area of modern cosmetics. In addition to coloring, the lightening of the natural hair color, or hair bleaching, is a very specific desire of many consumers since a blonde hair color is regarded as attractive and desirable in terms of fashion. A variety of hair-bleaching agents, with differing hair-bleaching performance, are available on the market for this purpose.

The oxidizing agents included in hair-bleaching agents are capable of lightening hair fibers by oxidative destruction of the hair's own melanin dye. For a moderate hair-bleaching effect it is sufficient to use hydrogen peroxide—optionally with the use of ammonia or other alkalizing agents—as the only oxidizing agent; to achieve a stronger hair-bleaching effect it is usual to use a mixture of hydrogen peroxide and peroxodisulfate salts and/or peroxomonosulfate salts.

For stability reasons, commercially available hair-bleaching agents are usually offered in two preparations packaged separately from one another, which are mixed together immediately before use to provide a completed preparation for use. Commercially available hair-bleaching agents usually consist of a liquid oxidizing agent preparation and a powder that includes solid oxidizing agents.

For hair bleaching, the powder that includes the solid oxidizing agents is mixed with the hydrogen peroxide solution immediately before use. This mixture is then applied to the hair and is rinsed out again after a contact time. In order to attain a sufficient hair-bleaching effect, agents of this type are usually made heavily alkaline; the pH value here lies between 9 and 10.5. High pH values of this kind are necessary to ensure an opening of the outer cuticle layer (cuticula) and thus enable a penetration of the active species (hydrogen peroxide and persulfates) into the hair.

In the case of human hair, trace elements such as copper, iron and zinc can become concentrated. Heavily bleached hair or damaged hair demonstrates an increased affinity to absorb trace elements.

The accumulation of metal ions in the hair fibers can also be caused by drinking water. In some southern European countries and also in some regions of the USA, water that includes high quantities of metal ions is used for daily bodily hygiene. Certain living conditions, however, such as the necessary administration of drugs such as cisplatin in the case of cancer therapy, increase the metal content in the body. The medical prescription of iron preparations to be taken during pregnancy or in the case of heavy menstrual bleeding as well as zinc preparations as agents to help combat dermatitis is routine practice. The daily administration of dietary supplements based on mineral substances forms part of a healthy lifestyle for some people.

These factors are potential sources that could lead to an accumulation of trace elements/metal ions above the necessary essential level in the body and ultimately in hair.

The metal ions concentrated in the hair fibers can catalyze the decomposition of the hydrogen and persulfates, which leads to an undesirable development of heat.

U.S. Pat. No. 5,635,167 thus proposes a method for removing metal ions such as copper or iron, in which a solution that includes 4 to 25 wt. % of a chelating agent and having a pH value from 4 to 9 is used.

EP 1714634 A1 describes hair-treatment kits for coloring human hair, comprising a first compartment, which includes a complexing agent, and a second compartment, which includes coloring agents. Here as well, undesirable reactions on and with hair that lead to an undesirable heating are prevented.

It has been found, however, that an undesirably high development of heat can still occur also in hair-bleaching agents that include complexing agents.

There is still a need to provide hair-bleaching agents which, when used, reduce the development of heat and the resultant damage to hair and/or the scalp.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for lightening keratinic fibers includes at least two preparations (A) and (B) packaged separately from one another, as well as optionally a further preparation (C) packaged separately from (A) and (B), which are mixed immediately before use to provide a mixture for use, wherein preparation (A) includes at least one persulfate, and preparation (B) is flowable and includes at least one oxidizing agent, characterized in that preparation (A) also includes at least one polysaccharide and at least one complexing agent.

A method for lightening keratinic fibers is characterized in that at least two preparations (A) and (B) are packaged separately from one another, of which preparation (A) includes at least one persulfate, a polysaccharide and a complexing agent, and preparation (B) includes at least one oxidizing agent, and are mixed to provide a mixture for use, which is applied to the fibers and is rinsed out again after a contact time.

A polysaccharide and at least one complexing agent are included in a preparation (A), which is part of an agent for lightening keratinic fibers, which includes at least two preparations (A) and (B) packaged separately from one another, as well as optionally a further preparation (C) packaged separately from (A) and (B), which are mixed immediately before use to provide a mixture for use, wherein preparation (A) includes at least one persulfate, and preparation (B) is flowable and includes at least one oxidizing agent, and the preparation is used to reduce damage to hair and/or the scalp, and/or to reduce the amount of heat produced when lightening keratinic fibers.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The problems described above are solved by agents for lightening keratinic fibers, which includes at least two preparations (A) and (B) packaged separately from one another, as well as optionally a further preparation (C) packaged separately from (A) and (B), which are mixed immediately before use to provide a mixture for use, wherein i. preparation (A) includes at least one persulfate, and
ii. preparation (B) is flowable and includes at least one oxidizing agent, and preparation (A) also includes at least one polysaccharide and at least one complexing agent.

"Keratinic fibers" or also "keratin fibers" are to be understood in this context as furs, wool, feathers, and in particular human hair. Although the agents according to the invention are suitable principally for lightening keratin fibers, nothing in principle conflicts with use in other fields as well.

The preparations (A) are preferably powdered. Powders consisting of solid constituents having different particle sizes can be used. It can usually be preferred, however, if the powders exhibit the most homogeneous possible particle size, in particular in order to facilitate uniform dispersion or dissolution of the powders in the preparations (B).

Preparations (A) can include the active substances in a solid cosmetic carrier. A solid cosmetic carrier can include salts of silicic acid, in particular salts of silicates and metasilicates with ammonium, alkali metals, and alkaline earth metals. Metasilicates in particular, which in accordance with the formula $(SiO_2)_n(M_2O)_m$, where M denotes an ammonium ion, alkali metal, or half a stoichiometric equivalent of an alkaline earth metal, are notable for a ratio between n and m of ≤1 and can be construed as a chain-like polymeric structures of the $[SiO_3]^{2-}$ anion, can be used with preference. Sodium metasilicate of the formula $[Na_2SiO_3]_\infty$, is particularly preferred in this context. Likewise preferred are those silicates that are constituted from a silicate of the formula $(SiO_2)_n(Na_2O)_m(K_2O)_p$, where n denotes a positive rational number and m and p, mutually independently, denote a positive rational number or 0, with the provisions that at least one of the parameters m or p is different from 0, and the ratio between n and the sum of m and p is between 2:1 and 4:1.

The solid cosmetic carriers can furthermore include what are known as pouring aids, which are intended to prevent clumping or caking of the powder constituents. Preferred appropriate pouring aids of this kind are water-insoluble, hydrophobizing, or moisture-absorbing powders of diatomaceous earth, pyrogenic silicic acids, calcium phosphate, calcium silicates, aluminum oxide, magnesium oxide, magnesium carbonate, zinc oxide, stearates, fatty amines, and the like.

Lastly, the solid cosmetic carriers can also additionally include a dedusting agent that prevents the powdered constituents from forming dust. Inert oils, in particular, can be used for this. The solid cosmetic carriers preferably include ester oils or mineral oils, preferably hydrocarbon oils such as liquid paraffin oil, as a dedusting agent.

Preparation (A) includes at least one persulfate salt as a first essential ingredient. Suitable persulfate salts suitable are inorganic peroxo compounds. These are preferably selected from ammonium peroxodisulfate, alkali metal peroxodisulfates, ammonium peroxomonosulfate, alkali metal peroxomonosulfates, alkali metal peroxodiphosphates, and/or alkaline earth metal peroxides. Ammonium peroxodisulfate and/or alkali metal peroxodisulfates are particularly preferred.

In a preferred embodiment of the present invention, preparation (A) includes as a persulfate salt at least one peroxodisulfate salt, in particular selected from ammonium peroxodisulfate and/or potassium peroxodisulfate and/or sodium peroxodisulfate and/or potassium hydrogen peroxomonosulfate.

It has also proven to be particularly preferred if the preparations (A) include at least two different peroxodisulfates. Preferred peroxodisulfate salts in this context are combinations of ammonium peroxodisulfate with potassium peroxodisulfate and/or sodium peroxodisulfate.

The preparations (A) include persulfate salts by preference in a quantity from 0.1 to 80 wt. %, preferably from 2 to 60 wt. %, particularly preferably from 3 to 50 wt. %, and in particular from 5 to 45 wt. %, based in each case on the total weight of the preparation (A).

As second essential ingredient, the preparations (A) include a polysaccharide. Polysaccharides, on account of the removal of unbound water, are able to increase the viscosity of a liquid.

In a preferred embodiment the preparation (A) includes a cellulose derivative as polysaccharide. This cellulose derivative is preferably selected from the group consisting of methylcellulose, ethyl cellulose, propyl cellulose, methyl ethyl cellulose, carboxymethyl cellulose, ethyl carboxymethyl cellulose, hydroxyethyl cellulose, hydroxypropyl cellulose, carboxymethyl hydroxyethyl cellulose, methyl hydroxyethyl cellulose, hydroxypropyl methylcellulose, ethyl hydroxyethyl cellulose, methyl ethyl hydroxyethyl cellulose, and mixtures of these compounds. It has been found that in particular the use of carboxymethyl cellulose as polysaccharide leads to a significant reduction of the amount of heat produced when lightening keratinic fibers enriched with metal ions.

Carboxymethyl celluloses (CMCs) are cellulose ethers in which some of the hydroxyl groups are linked as ethers to a carboxymethyl group (—$CH_2$—COOH). Carboxymethyl celluloses are insoluble in water in their acid form. Accordingly, the sodium salt of a carboxymethyl cellulose is most preferably used as polysaccharide in the preparation (A).

Suitable sodium-carboxymethyl celluloses are obtainable for example under the names "Aqualon" or "Blanose" from Ashlan Inc. or under the name "Cekol®" from CP Kelco.

It is also preferable if preparation (A)—based on its weight—includes polysaccharide in an amount from 0.5 to 5.0 wt. %, preferably from 1.0 to 4.0 wt. %, and particularly preferably from 1.5 to 3.0 wt. %.

As further compulsory ingredient, preparation (A) includes at least one complexing agent. The at least one complexing agent is preferably selected from the group consisting of (a) nitrilotriacetic acid (NTA),
(b) diethylenetriaminepentaacetic acid (DPTA),
(c) ethylenediaminedisuccinic acid (EDDS),
(d) ethylenediaminediglutaric acid (EDGA),
(e) 2-hydroxypropylenediaminedisuccinic acid (HPDS),
(f) glycinamide-N—N'-disuccinic acid (GADS),
(g) ethylenediamine-N—N'-diglutaric acid (EDDG),
(h) 2-hydroxypropylenediamine-N—N'-disuccinic acid (HPDDS),
(i) ethylenediaminetetraacetic acid (EDTA),
(j) ethylenedicysteic acid (EDC),
(k) diaminoalkyldi(sulfosuccinic acid) (DDS),
(l) ethylenediamine-N—N'bis(ortho-hydroxyphenylacetic acid (EDDHA),
(m) N-2-hydroxyethyl-N,N-diacetic acid,
(n) glyceryliminodiacetic acid, (o) iminodiacetic acid-N-2-hydroxypropylsulfonic acid,
(p) aspartic acid-N-carboxymethyl-N-2,5-hydroxypropyl-3-sulfonic acid,
(q) β-alanine-N,N'-diacetic acid,
(r) aspartic acid-N,N'-diacetic acid,
(s) aspartic acid-N-monoacetic acid,
(t) dipicolinic acid,
(u) 1-hydroxyethane-(1,1-diphosphonic acid) (HEDP),
(v) and salts and/or derivatives thereof.

With regard to the reduction of the amount of heat produced when lightening keratinic fibers enriched with metal ions, the use of a salt, preferably a sodium salt, of ethylenediaminetetraacetic acid (EDTA) in preparation (A) has proven to be particularly advantageous. Suitable EDTA salts include, for example, disodium ethylenediaminetetraacetate ($Na_2H_2EDTA$), tetrasodiumethylenediaminetetraacetate ($Na_4EDTA$), and calcium disodiumethylenediaminetetraacetate ($CaN_2EDTA$), wherein disodium ethylenediaminetetraacetate is preferred.

1-hydroxyethane-(1,1-diphosphonic acid) (HEDP) is a complexing agent that likewise is preferred.

In a most preferred embodiment, preparation (A) includes—based on its weight—complexing agents in an amount greater than 0.6 wt. %, preferably in amounts from 0.8 to 2.5 wt. %, more preferably from 1.0 to 2.2 wt. %, and most preferably from 1.2 to 2.0 wt. %.

Without being bound to this theory, the ingredients of the ready-to-use agent according to the invention are immobilized by the addition of a polysaccharide, and in particular the decomposition of the hydrogen peroxide catalyzed by metal ions is slowed relative to the complexing of the metal ions by the complexing agent.

Preparations (B) and, as appropriate, (C) include the active substances in a flowable cosmetic carrier. The basis of the flowable cosmetic carrier is preferably aqueous or aqueous alcoholic. For purposes of hair bleaching, such carriers are, for example, gels or also surfactant-containing foaming solutions such as shampoos, foam aerosols, or other preparations that are suitable for use on the hair A preferred flowable carrier includes, in the context of the invention, at least 40 wt. %, in particular at least 50 wt. % water. "Aqueous alcoholic" carriers are to be understood in the context of the present invention as water-containing compositions including 3 to 70 wt. % of a $C_1$ to $C_4$ alcohol, in particular ethanol or isopropanol. The preparations (B) and, as appropriate, (C) can each additionally include further organic solvents, for example methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred in this context.

Preparations (B) include hydrogen peroxide as oxidizing agents.

The concentration of a hydrogen peroxide solution in preparation (B) is defined on the one hand by legal requirements and on the other hand by the desired effect.

The preparations (B) include, based on their weight, hydrogen peroxide in amounts by preference from 0.5 to 30 wt. %, preferably from 1 to 20 wt. %, particularly preferably from 5 to 15 wt. %, and particularly preferably 6 to 12 wt. %, explicitly 6, 7, 8, 9, 10, 11, or 12 wt. %.

Preferred ready-to-use agents are characterized in that they include, based on the total weight of the ready-to-use agent, 0.01 to 12 wt. %, by preference 0.1 to 10 wt. %, particularly preferably 3 to 9 wt. % hydrogen peroxide.

The ready-to-use agents for lightening keratinic fibers are produced immediately before application to the hair by mixing the two preparations (A) and (B) and optionally a third preparation (C) and/or further preparations. The consistency of the ready-to-use agents ranges from flowable to unspreadable.

The viscous properties of preparation (B) are of importance for the good miscibility and high stability thereof. The preparations (B) therefore preferably have a viscosity from 1,000 mPa·s to 50,000 mPa·s, preferably from 5,000 mPa·s to 45,000 mPa·s, and particularly preferably from 7,000 mPa·s to 40,000 mPa·s, measured using a rotational viscometer from Brookfield, spindle size 4, at 25° C. and 4 rpm. The finished, mixed and ready-to-use agents preferably have a viscosity from 10,000 mPa·s to 100,000 mPa·s and particularly preferably from 18,000 mPa·s to 80,000 mPa·s, measured using a rotational viscometer from Brookfield, spindle size 5, at 25° C. and 4 rpm.

The agents according to the invention can include further active substances and auxiliaries. These will be described hereinafter.

It can be advantageous if preparation (B) includes at least one non-ionic surfactant, preferably at least one ethoxylated fatty alcohol with 40 to 60 ethylene oxide units. This is to be understood as an addition product of ethylene oxide with a fatty alcohol. Fatty alcohols are, in this context, saturated and unsaturated alcohols having 12 to 24 C atoms, which can be linear or branched. The molar quantity of ethylene oxide that was used per mol of fatty alcohol is understood to designate the degree of ethoxylation. Suitable in this context as a non-ionic surfactant are, in particular, ethylene oxide addition products with octyl alcohol (capryl alcohol), nonyl alcohol (pelargonyl alcohol), undecyl alcohol, undec-10-en-1-ol, dodecyl alcohol (lauryl alcohol), 2,6,8-trimethyl-4-nonanol (isolauryl alcohol), tridecyl alcohol, tetradecyl alcohol (myristyl alcohol), pentadecyl alcohol, hexadecyl alcohol (cetyl/palmityl alcohol), heptadecyl alcohol, octadecyl alcohol (stearyl alcohol), isostearyl alcohol, (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), nonadecan-1-ol (nonadecyl alcohol), eicosan-1-ol (eicosyl alcohol/arachyl alcohol), (9Z)-eicos-9-en-1-ol (gadoleyl alcohol), (5Z,8Z,11Z,14Z)-eicosa-5,8,11,14-tetraen-1-ol (arachidonyl alcohol), heneicosyl alcohol, docosyl alcohol (behenyl alcohol), (13Z)-docos-13-en-1-ol (erucyl alcohol), or (13E)-docosen-1-ol (brassidyl alcohol). It is likewise possible to use mixtures of fatty alcohols that occur by deliberate mixing or also as a result of recovery methods. Examples are coconut alcohol (mixture of $C_8$-$C_{18}$ fatty alcohols) or cetearyl alcohol (1:1 mixture of $C_{16}$ and $C_{18}$ fatty alcohols).

Degrees of ethoxylation from 20 to 60 are preferred. Non-ionic surfactants of the ethoxylated fatty alcohol type that are preferred are ceteareth-20 and ceteareth-50.

The setting of the pH value of the finished, mixed and ready-to-use agent according to the invention is also of importance for the lightening performance. Finished, mixed and ready-to-use agents of which the pH value is between 9 and 12 are preferred.

The agents according to the invention can furthermore therefore include alkalizing agents. Preferred alkalizing agents are, for example, ammonia, alkanolamines, basic amino acids, as well as inorganic alkalizing agents such as alkali/alkaline earth metal hydroxides, alkali/alkaline earth metal metasilicates, alkali/alkaline earth metal silicates, alkali/alkaline earth metal phosphates, and alkali/alkaline earth metal hydrogen phosphates. Lithium, sodium, and/or potassium preferably serve as metal ions. Preferred alkalizing agents are alkali/alkaline earth metal metasilicates and alkali/alkaline earth metal silicates.

Suitable inorganic alkalizing agents are preferably selected from sodium hydroxide, potassium hydroxide, calcium hydroxide, barium hydroxide, sodium phosphate, potassium phosphate, sodium silicate, potassium silicate, magnesium silicate, sodium carbonate, and potassium carbonate. Sodium hydroxide and/or potassium hydroxide are particularly preferred.

Alkanolamines as alkalizing agents are preferably selected from alkanolamines of primary, secondary, or tertiary amines having a $C_2$-$C_6$ alkyl basic structure that carries at least one hydroxyl group. Particularly preferred alkanolamines are selected from the group that is constituted from 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, methylglucamine, triethanolamine, diethanolamine, and triisopropanolamine. Particularly preferred alkanolamines are monoethanolamine, 2-amino-2-methylpropanol, and triethanolamine.

Basic amino acids as alkalizing agent are preferably selected from the group that is constituted from L-arginine, D-arginine, D/L-arginine, L-lysine, D-lysine, D/L-lysine, L-ornithine, D-ornithine, D/L-ornithine, L-histidine, D-histidine, and/or D/L-histidine. L-arginine, D-arginine, and/or D/L-arginine are particularly preferably used as an alkalizing agent.

The preparations (A) and (B) can be mixed with further separately packaged preparations immediately prior to use so as to provide a mixture for use.

In a preferred embodiment of the invention, the agent additionally includes at least one further preparation (C) packaged separately from preparations (A) and (B), preparation (C) including at least one alkalizing agent.

Regardless of whether preparation (C) and/or preparation (B) and/or further preparations include alkalizing agents, if alkalizing agents are used, those agents according to the invention that include alkalizing agents in a quantity from 0.05 to 20 wt. %, in particular from 0.5 to 10 wt. %, based in each case on the total weight of the entire agent according to the invention, are preferred.

To further enhance the lightening performance, a silicon-containing compound can additionally be added to preparation (C) as a bleach intensifier. Said compound is preferably selected from the group that is constituted from silicic acid, alkali metal silicates, and alkaline earth metal silicates.

It is particularly advantageous when, in order to suppress undesired residual color impressions, particularly in the reddish or bluish range, the lightening or hair-bleaching agents include specific substantive dyes of the complementary colors. These are dyes that absorb directly onto the hair and do not require an oxidative process in order to form the color. Substantive dyes are usually nitrophenylenediamines, nitroaminophenols, azo dyes, anthraquinones, or indophenols. Substantive dyes are known as anionic, cationic, and non-ionic substantive dyes. The substantive dyes are respectively used preferably in a quantity from 0.001 to 2 wt. %, based on the entire preparation for use.

The agents can also include further active substances, auxiliaries and additives, such as non-ionic polymers, cationic polymers, anionic polymers, zwitterionic and amphoteric polymers, structuring agents, further hair-conditioning compounds, further active substances improving fiber structure, further surfactants, dyes for coloring the agent according to the invention, anti-dandruff active substances, amino acids, oligopeptides, animal- and/or plant-based protein hydrolyzates, light-protection agents, UV blockers, vitamins, provitamins, vitamin precursors, plant extracts, fats, waxes, swelling and penetration substances, opacifiers, pearlescent agents, thickeners and pigments.

A second subject of the invention is a method for changing the color of keratinic fibers, characterized in that at least two preparations (A) and (B) packaged separately from one another, of which preparation (A) includes at least one persulfate, a polysaccharide and a complexing agent, and preparation (B) includes at least one oxidizing agent, are mixed to provide a mixture for use, which is applied to the fibers and is rinsed out again after a contact time.

The ready-to-use agents are produced, immediately before application to the hair, by mixing the two preparations (A) and (B) and optionally a third preparation (C) and/or further preparations. In the case of ready-to-use agents that are mixed from more than two preparations to provide a completed mixture for use, it can be irrelevant whether firstly two preparations are mixed with one another and then the third preparation is added and mixed in, or whether all the preparations are combined together and then mixed. Mixing can be accomplished by stirring in a dish or cup, or by shaking in a closable container.

The term "immediately" is to be understood as a time period from a few seconds to one hour, by preference up to 30 minutes, in particular up to 15 minutes.

The agents according to the invention are used in a method for lightening keratinic fibers, in particular human hair, in which the agent is applied to the keratin-containing fibers, left on the fibers for a contact period from 10 to 60 minutes, and then rinsed out again with water or washed out with a shampoo.

The contact time of the ready-to-use lightening agents is preferably 10 to 60 minutes, in particular 15 to 50 minutes, particularly preferably 20 to 45 minutes. During the contact time of the agent on the fibers, it can be advantageous to assist the lightening process by delivering heat. Heat delivery can occur by way of an external heat source, for example using a warm air blower, and also, in particular in the case of a hair lightening process on living subjects, by way of the body temperature of the subject. With the latter option, the portion to be lightened is usually covered with a hood. A contact phase at room temperature is preferred.

After the contact time has ended, the remaining lightening preparation is rinsed out of the hair with water or with a cleaning agent. A commercially available shampoo can, in particular, serve as a cleaning agent in this context, wherein in particular the cleaning agent can then be omitted and the rinsing-out operation can occur using tap water if the lightening agent possesses a carrier with a high surfactant content.

The above-described preferred embodiments of the agent also apply, mutatis mutandis, to the method.

A further subject of the invention is the use of a polysaccharide and at least one complexing agent in a preparation (A), which is part of an agent for lightening keratinic fibers, including at least two preparations (A) and (B) packaged separately from one another, as well as optionally a further preparation (C) packaged separately from (A) and (B), which are mixed immediately before use to provide a mixture for use, wherein i. preparation (A) includes at least one persulfate, and
ii. preparation (B) is flowable and includes at least one oxidizing agent, to reduce damage to hair and/or the scalp, and/or
to reduce the amount of heat produced
when lightening keratinic fibers.

The above-described preferred embodiments of the agent also apply, mutatis mutandis, to the use.

The following examples are intended to explain the subject of the present invention, but in a non-limiting manner.

Examples

TABLE 1

Composition of preparations (A) for hair-bleaching agents consisting of two preparations

| Ingredient | E1 | E2 | V1 |
|---|---|---|---|
| $Na_2H_2EDTA$ | 0.6 | 2.0 | 0.6 |
| Sodiumhexametaphosphate | 0.3 | 0.3 | 0.3 |
| Sodium silicate | 36 | 36 | 36 |
| Aerosil 200 | 0.4 | 0.4 | 0.4 |
| Rohagit S hv | 1.0 | 1.0 | 1.0 |
| Cekol 50000 | 2.0 | 2.0 | — |
| Ammonium persulfate + 0.5% silicic acid | 10.0 | 10.0 | 10.0 |
| Potassium persulfate | 32 | 32 | 32 |
| Paraffinum Liquidum | 3.6 | 3.6 | 3.8 |
| Perfume | 0.5 | 0.5 | 0.5 |
| Dimethicone | 1.5 | 1.5 | 1.5 |
| Polyquaternium-4 | 0.3 | 0.3 | 0.3 |
| Dye | 0.1 | 0.1 | 0.1 |
| Magnesium carbonate | ad 100 | ad 100 | ad 100 |

*used raw materials: Aerosil 200 (INCI name: Silica (Evonik Degussa)), Rohagit S hv (INCI name: Acrylates Copolymer (Evonik Röhm)), Cekol 50000 (INCI name: Cellulose Gum (CP (Kelco))

TABLE 2

Composition of a preparation (B) for hair-bleaching agents consisting of two preparations

| Ingredient | B |
|---|---|
| Potash lye 4% techn. | 0.1 |
| Dipicolinic acid | 0.1 |
| Disodiumpyrophosphate | 0.03 |
| HEDP 60% | 1.5 |
| Hydrogen peroxide 50% | 18 |
| PEG-40 Castor Oil | 0.7 |
| Cetearyl Alcohol | 4.0 |
| Water, demineralized | ad 100 |

To produce a hair-bleaching agent, one of the preparations (A) was mixed in each case in a ratio of 1:2 with the preparation (B).

Hair damage tests by means of NIR analysis

Hair can be damaged by oxidative treatment, such as oxidative lightening.

Cysteine is a component of human hair. The disulfide bridge included in cysteine can be oxidatively broken during a hair treatment, and the resultant thiol can be converted by further oxidation into the sulfonic acid group of cysteic acid. The cysteic acid content of the hair thus changes.

The reduction of cysteine and the increase of cysteic acid thus constitute an indicator for hair damage and can be determined by means of NIR analysis.

To measure the damage to hair, the cysteic acid value of each treated hair strand was determined by quantitative NIR spectroscopy. The spectra were recorded using an MPA™ FT-NIR spectrometer from the company Bruker Optik GmbH. The infrared range includes the wave number range from 12,500 $cm^{-1}$ to 4000 $cm^{-1}$, and is characteristic for overtone and combination vibrations of CH, OH, and NH groups, for example.

The measurement of the samples was carried out using the integrated sphere module at six different sample positions in diffuse reflection. The wave number range from 7300 $cm^{-1}$ to 4020 $cm^{-1}$ was selected for the analysis of the measured NIR spectra.

The NIR spectra of cysteine show characteristic absorption bands in the wave number range from 6200 $cm^{-1}$ to 5500 $cm^{-1}$. If the hair changes due to relatively severe damage (i.e. the cysteic acid content in the hair increases), this has an effect in the NIR spectrum on the bands at 5020 $cm^{-1}$ to 4020 $cm^{-1}$, which are characteristic for cysteic acid. The NIR spectra were quantitatively evaluated by computer.

In order to damage and dope the hair strands, these were pre-bleached twice and then the dried hair strand was dipped for 1 minute in 20 ml of a solution that included copper ions (content of $Cu^{2+}$=200 ppm). The doping method was performed a total of three times.

The used hair strands were:

| | |
|---|---|
| H1: Kerling Euronaturhaar 6-0 | untreated |
| H2: Kerling Euronaturhaar 6-0 | pre-bleached twice with a hair-bleaching agent based on the preparation (A)-V1, doped with copper ions three times and subsequently bleached once with a bleaching agent based on preparation (A)-V1 |
| H3: Kerling Euronaturhaar 6-0 | pre-bleached twice with a hair-bleaching agent based on the preparation (A)-V1, doped with copper ions three times and subsequently bleached three times with a bleaching agent based on preparation (A)-V1 |
| H4: Kerling Euronaturhaar 6-0 | pre-bleached twice with a hair-bleaching agent based on the preparation (A)-E2, doped with copper ions three times and subsequently bleached once with a bleaching agent based on preparation (A)-E2 |
| H5: Kerling Euronaturhaar 6-0 | pre-bleached twice with a hair-bleaching agent based on the preparation (A)-E2, doped with copper ions three times and subsequently bleached three times with a bleaching agent based on preparation (A)-E2 |

In each case 3 strands of hair were produced and measured.

TABLE 3

NIR analysis values:

| Hair strands | Cysteic acid [wt. %] |
|---|---|
| H1 | 0.4 |
| H2 | 11.7 |
| H3 | 12.7 |
| H4 | 10.2 |
| H5 | 12.4 |

The results clearly show that the hair-bleaching agent according to the invention is less damaging to hair.

In addition, the maximum temperature and the total amount of heat produced, when bleaching hair, within 45 minutes of applying the particular hair-bleaching agent were determined. This determination was also carried out on hair strands that had been pre-bleached twice and doped three times with copper ions. The pre-bleaching was performed in each case with the hair-bleaching agent that was also used for the hair bleaching.

TABLE 4 maximum temperature and amount of
heat during the bleaching process

| Bleaching agent (mixing ratio) | $T_{max}$ [° C.] | Amount of heat |
|---|---|---|
| (A)-V1 + (B) (1:2) | 57 | 251 |
| (A)-E1 + (B) (1:2) | 45 | 319 |
| (A)-E2 + (B) (1:2) | 44 | 241 |

To determine the amount of heat, the temperature during the bleaching was determined over a period of 45 minutes and plotted in a graph over time. The area below the resultant curve was then determined up to a temperature of 30° C. This is proportional to the amount of heat produced.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, including at least two preparations (A) and (B) packaged separately from one another, which are mixed immediately before use to provide a mixture for use, wherein
    i) preparation (A) includes
        at least two different persulfates selected from the group consisting of ammonium peroxodisulfate, potassium peroxodisulfate, and sodium peroxodisulfate,
        carboxy methyl cellulose in an amount from 1.0 to 4.0 wt % based on total weight of preparation (A), and
        a complexing agent that is disodium ethylenediaminetetraacetate in an amount from 0.8 to 2.5 wt. % based on total weight of preparation (A), and
    ii) preparation (B) includes
        at least one oxidizing agent and
        at least one ethoxylated fatty alcohol with 40 to 60 ethylene oxide units,
        and has a viscosity of 7,000 to 40,000 mPa·s measured using a rotational viscometer from Brookfield, spindle size 4, at 25° C. and 4 rpm.

2. The agent according to claim 1, wherein the oxidizing agent includes hydrogen peroxide in amounts from 0.5 to 30 wt. %.

3. A method for lightening keratinic fibers includes mixing at least two preparations (A) and (B) according to claim 1, applying the mixed preparation (A) and preparation (B) to the keratinic fibers, and rinsing the keratinic fibers out after a contact time from 10 to 60 minutes.

* * * * *